United States Patent [19]

Parks

[11] Patent Number: 4,573,457

[45] Date of Patent: Mar. 4, 1986

[54] TOE LIFTING SHOE

[76] Inventor: Thomas J. Parks, 1826 E. Evergreen, Mesa, Ariz. 85203

[21] Appl. No.: 566,781

[22] Filed: Dec. 29, 1983

[51] Int. Cl.⁴ .............................................. A61F 5/00
[52] U.S. Cl. .................... 128/80 E; 36/31; 128/609
[58] Field of Search ............ 128/609, 612, 620, 80 E; 36/31, 33

[56] References Cited

U.S. PATENT DOCUMENTS

| | | | |
|---|---|---|---|
| 634,588 | 10/1899 | Roche | 128/620 |
| 1,542,210 | 6/1925 | Bonaba | 128/620 |
| 2,001,203 | 5/1935 | Kushinsky | 128/620 |
| 2,440,894 | 5/1948 | Caesar | 128/80 E |
| 2,468,244 | 9/1947 | Roles | 128/609 |
| 2,517,472 | 8/1950 | Fathauer | 36/33 |
| 2,522,515 | 9/1950 | Hill | 36/33 |
| 3,585,993 | 6/1971 | Heedly | 128/80 |
| 4,177,582 | 12/1979 | Ehrlich, Jr. | 36/33 |
| 4,331,152 | 5/1982 | Bartoli | 128/591 |
| 4,400,894 | 8/1983 | Ehrlich | 36/33 |

FOREIGN PATENT DOCUMENTS

| | | | |
|---|---|---|---|
| 168194 | 4/1951 | Austria | 128/620 |
| 397582 | 6/1924 | Fed. Rep. of Germany . | |
| 358247 | 9/1982 | Fed. Rep. of Germany . | |
| 28286 | of 1902 | United Kingdom | 128/609 |
| 15329 | of 1913 | United Kingdom | 128/620 |
| 433573 | 8/1935 | United Kingdom | 128/620 |

Primary Examiner—Paul J. Hirsch
Attorney, Agent, or Firm—Cahill, Sutton & Thomas

[57] ABSTRACT

A flexible strip divides a shoe sole into toe and instep sections. Toe deflection means lifts the toe section when the shoe is in a weighted state. Toe deflection means includes a toe plate coupled to the toe section of the sole and an instep plate coupled to the instep section of the sole. The toe deflection means pivots the toe section of the sole about the flexible strip by applying bending forces to the toe and instep sections of the sole.

2 Claims, 7 Drawing Figures

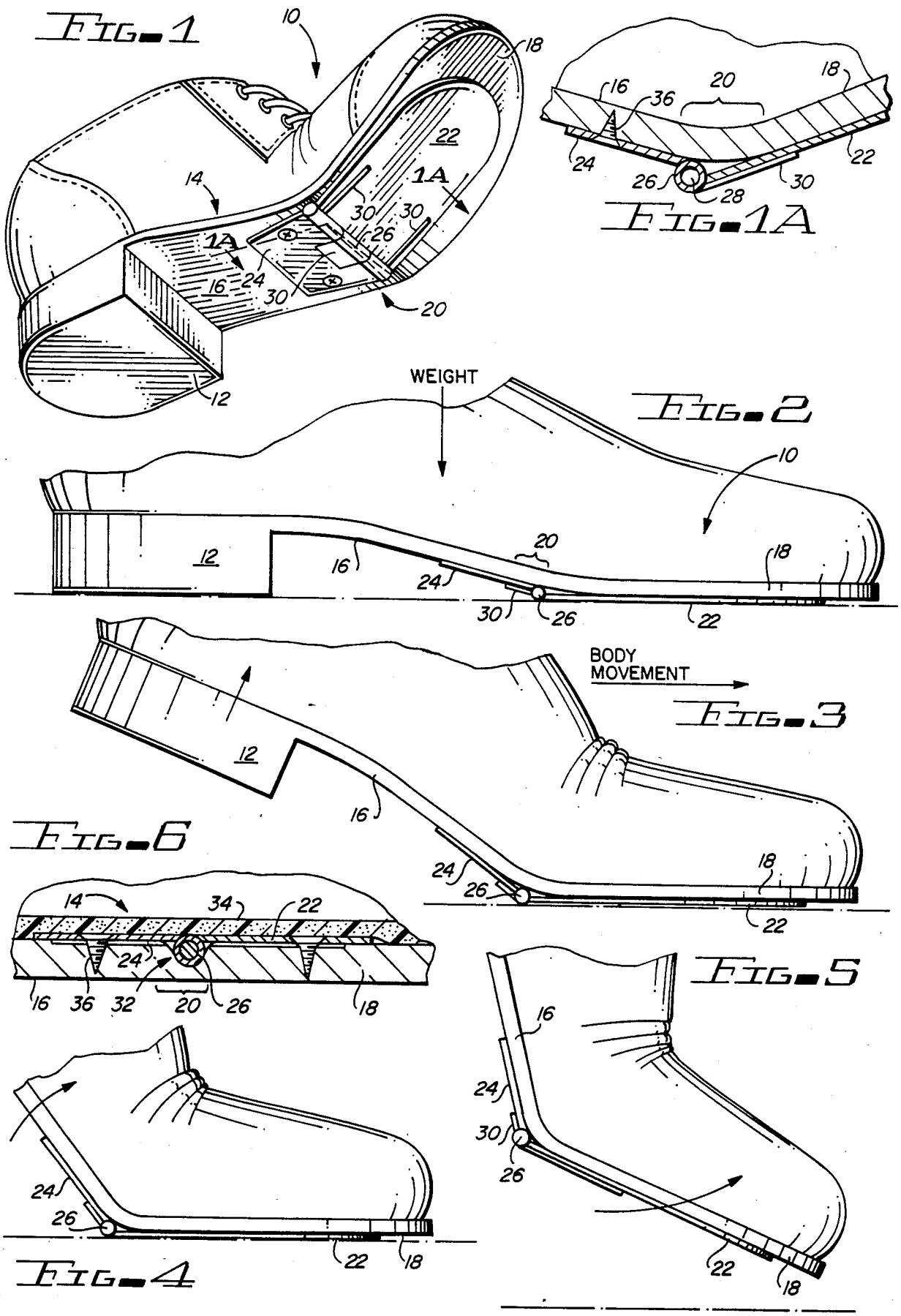

TOE LIFTING SHOE

BACKGROUND OF THE INVENTION

1. Field of the Invention

This invention relates to orthopedic shoes, and more particularly to orthopedic shoes capable of lifting the tow section of the shoe when the shoe is in an unweighted state.

2. Description of the Prior Art

A person suffering from a condition known as "dropfoot" is unable to voluntarily pivot the foot around the ankle joint or to raise his toes while walking. Various types of prior art devices have attempted to mechanically produce the appropriate ankle rotation or toe lift.

U.S. Pat. No. 4,331,152 (Bartoli) discloses an orthopedic shoe having a flexible metal plate concealed between the various layers of the shoe sole. The rear end of the metal plate is connected by a link to a coiled spring deflection assembly positioned within a hollowed out chamber in the heel. The application of spring force to the plate erects the tip of the shoe with or without rotation.

U.S. Pat. No. 2,440,894 (Ceaser) discloses a spring-biased ankle rotation device having one end coupled to the calf of the wearer's leg and the opposing end coupled to the instep of the shoe. A spring positioned in the instep region of the shoe immediately in front of the heel causes rotation of the entire shoe about the wearer's ankle joint.

U.S. Pat. No. 3,585,993 (Heedly) discloses yet another device which rotates a wearer's foot about his ankle joint. This device includes a spring loaded axle positioned within a lateral passageway in the heel of the wearer's shoe. A first arm is coupled to the heel of the wearer's shoe and the second arm is coupled to the instep of the wearer's shoe. Unweighting of the shoe pivots the shoe around the wearer's ankle joint.

German Pat. Nos. 358,247 (Betz) and 397,582 (Brebeck) disclose other shoe-mounted devices for rotating a wearer's shoe around his ankle joint.

SUMMARY OF THE INVENTION

It is therefore a primary object of the present invention to provide a toe lifting shoe which causes the toe section of the shoe sole to pivot upward about the flexible strip which separates the toe section from the instep section of the sole.

Another object of the present invention is to provide a toe lifting shoe including a toe deflection means in the form of a hinged plate centered about the flexible strip of the shoe sole.

Yet another object of the present invention is to provide a toe lifting shoe which can be fabricated by attaching toe deflection means to an existing conventional shoe.

Still another object of the present invention is to provide a toe lifting shoe which can provide a controlled amount of upward biasing force by selection of an appropriate biasing spring.

Still another object of the present invention is to provide a toe lifting shoe utilizing toe deflection means which can be coupled either to the upper or lower surface of the shoe sole.

Briefly stated, and in accord with one embodiment of the invention, a toe lifting shoe includes a heel and a sole deflectable about a flexible strip which divides the sole into a toe section and an adjacent instep section. Toe deflection means having a toe plate coupled to the toe section of the sole and an instep plate coupled to the instep section of the sole lifts the toe section when the shoe is in an unweighted state and enables the toe section to be levelled when the shoe is in a weighted state. The toe deflection means operates by causing the toe section of the shoe to pivot about the flexible strip by applying bending forces to the toe and instep sections of the sole.

DESCRIPTION OF THE DRAWINGS

The invention is pointed out with particularity in the appended claims, however, other objects and advantages together with the operation of the invention may be better understood by reference to the following detailed description taken in connection with the following illustrations, wherein:

FIG. 1 is a perspective view of the toe lifting shoe of the present invention.

FIG. 1A is an enlarged sectional view of the toe deflection means illustrated in FIG. 1, taken along section line 1A—1A.

FIG. 2 is a partially cutaway elevational view of the toe lifting shoe illustrated in FIG. 1, particularly illustrating the shoe in the weighted state where the shoe sole is in the level position.

FIG. 3 is a partially cutaway elevational view of the toe lifting shoe illustrated in FIG. 1, particularly illustrating the shoe transitioning from the weighted state to the unweighted state.

FIG. 4 is a partially cutaway sectional view of the toe lifting shoe illustrated in FIG. 3, particularly illustrating nearly completed transition from the weighted to the unweighted state.

FIG. 5 is a partially elevational view showing the toe-lifting shoe of the present invention in the unweighted state.

FIG. 6 is a partially cutaway view of the toe-lifting shoe particularly illustrating the toe deflection means coupled to the upper surface of the shoe sole.

DESCRIPTION OF THE PREFERRED EMBODIMENT

In order to better illustrate the advantages of the invention and its contributions to the art, a preferred hardware embodiment of the invention will now be described in detail.

Referring now to FIGS. 1, 1A and 2, a toe-lifting shoe 10 includes a conventional heel 12 and a sole 14. Sole 14 is divided into an instep section 16 and a toe section 18 by a conventional flexible strip 20.

The toe deflection means of the present invention includes a toe plate 22 rigidly coupled to a selected area of toe section 18. An instep plate 24 is rigidly coupled to a predetermined area of instep section 16. A centrally located hinge section 26 includes a hinge pin 28 and serves to rotatably couple together toe plate 22 and instep plate 24.

Biasing means in the form of a spring 30 is concentrically wound around hinge pin 28 and contacts the lower surface of toe plate 22 and instep 24 to thereby apply a bending or biasing force which tends to maintain toe section 18 of the sole 14 in an upwardly biased or raised position as particularly illustrated in FIG. 1.

FIG. 2 illustrates that when a wearer steps down on his foot, the transition from the unweighted state depicted in FIG. 1 to the weighted state depicted in FIG.

2 causes toe section 18 to overcome the upwardly biasing force exerted by spring 26 and deflects toe section 18 downward into the levelled or weighted state depicted in FIG. 2. The thickness of sole 14, the material from which the sole is fabricated, the wearer's size and weight and various other factors determine the type, size and strength of the spring utilized to provide the biasing force for the toe deflection means of the present invention. Spring 30 must exert a sufficient biasing force on the toe deflection means that it have the capability of deflecting shoe 10 into the lifted condition depicted in FIG. 1 while still enabling the application of the wearer's weight to shoe 10 to deflect shoe 10 downward into the levelled condition depicted in FIG. 2.

FIGS. 3, 4 and 5 depict the transition of shoe 10 from the levelled state illustrated in FIG. 2 to the lifted or unweighted state depicted in FIG. 5. Reimposing the weight of the wearer's foot on shoe 10 during normal walking operations will cause shoe 10 to transition back into the levelled state depicted in FIG. 2. FIG. 6 specifically indicates that the toe deflection means of the present invention can also be coupled to the upper interior surface of sole 14 by boring out a channel 32 from the upper surface of sole 14 to provide a receptacle for hinge pin 28 of the toe deflection means. A foam insole 34 or similar material may be positioned above the toe deflection means to provide sufficient isolation between plates 22 and 24 and the lower surface of the wearer's foot.

FIG. 1 and 6 both indicate that toe plate 22 and instep plate 24 may be coupled to the sole of the wearer's shoe by securing means such as screws. Numerous other types of securing means are readily available to secure the toe deflection means to sole 14 as would be readily apparent to one of ordinary skill in the art.

In operation, the toe deflection means of the present invention causes the toe section of the wearer's shoe to transition from the levelled state into the lifted state as the shoe is unweighted. The toe lifting shoe of the present invention assumes the fully lifted position as the wearer's retreating foot is completely unweighted permitting the wearer to advance that foot while maintaining the maximum shoe to ground clearance permitted by the lifted or elevated position of toe section 18 of shoe 10. As the wearer's foot transitions from the unweighted position to the weighted position as the wearer's forward translation continues, toe 18 of shoe 10 transitions from the lifted or unweighted state to the levelled or weighted state as indicated by the reverse progression of FIGS. 5, 4, 3 and 2. In practice, the present invention has been found to successfully achieve the results achieved by the far more complex and cumbersome devices recited in the Background of the Invention. The toe deflection means of the present invention can be readily attached to an existing shoe by the very straightforward procedure of installing four screws to mount toe plate 22 and instep plate 24 to the appropriate section of sole 14.

Numerous different versions of the preferred embodiment of the present invention would be readily apparent to one of ordinary skill in the art. For example, toe plate 22 and instep plate 24 may assume many different lengths and widths while still serving functions equivalent to those described above. In addition, hinge 26 could assume many different configurations other than the familiar standardized configurations depicted in the drawings while still serving to pivotally interconnect toe plate 22 with instep plate 24. Similarly, spring 26, rather than being helically wrapped around hinge pin 28, might be configured as biasing means taking the form of a section of spring steel coupled either above or below plates 22 and 24 to provide an upward biasing force in a manner equivalent to that provided by the helically wound spring 26 depicted in the drawings. Numerous other substitutions of such equivalent components would readily be apparent to one of ordinary skill in the art. Accordingly, it is intended by the appended claims to cover all such modifications of the invention which fall within the true spirit and scope of the invention.

I claim:

1. A toe-lifting show comprising a heel and a sole deflectable about a linear, flexible strip extending transversely across the sole and dividing the sole into a toe section having an upwardly sloping rear surface and an adjacent instep section comprising:
   a. a flat, rigid toe plate coupled by securing means to the lower surface of the toe section of the sole and inclduing a linear rear surface extending transversely across the sole in proximity to the flexible strip;
   b. a flat, rigid instep plate coupled by securing means to the lower surface of the instep section of the sole and including a linear front surface extending transversely across the sole in proximity to the flexible strip with a gap disposed between the linear front surface of the instep plate and the linear rear surface of the toe plate;
   c. a hinge having a cylindrical body positioned within said gap and oriented parallel to the adjacent linear surface of the toe plate and instep plate for pivotally interconnecting the toe and instep plates, the cylindrical body of the hinge further including a cylindrical aperture for receiving a hinge pin; and
   d. a spring coupled to the hinge, surrounding the hinge pin, and including a first spring element extending outward from the hinge to engage the toe plate and a second spring element extending outward from the hinge to engage the instep plate for upwardly biasing the toe plate with respect to the instep plate and for angularly deflecting the toe section of the shoe with respect to the instep section of the shoe along the flexible strip, whereby the spring acting on the toe and instep plates upwardly pivots the toe section with respect to the instep section without angularly deflecting the instep section when the shoe is in an unweighted state and permits the toe section to be downwardly pivoted with respect to the instep section when the shoe is in a weighted state, wherein the cylindrical body of the hinge and the flexible strip are positioned within the upwardly sloping rear surface of the toe section to avoid transferring substantial forces between a flat walking surface and the sole.

2. The toe-lifting shoe of claim 1 wherein said spring is coaxially wound around said hinge pin.

* * * * *